United States Patent

Haughey

(10) Patent No.: US 6,579,227 B2
(45) Date of Patent: Jun. 17, 2003

(54) FORESKIN RESTORATION DEVICE

(76) Inventor: James A. Haughey, 2421 Clark Ave., Venice, CA (US) 90291

( * ) Notice: Subject to any disclaimer, the term of this patent is extended or adjusted under 35 U.S.C. 154(b) by 0 days.

(21) Appl. No.: 09/844,956

(22) Filed: Apr. 26, 2001

(65) Prior Publication Data

US 2001/0049468 A1 Dec. 6, 2001

Related U.S. Application Data

(60) Provisional application No. 60/200,119, filed on Apr. 27, 2000.

(51) Int. Cl.$^7$ ................................................. A61F 5/00
(52) U.S. Cl. ........................................................ 600/38
(58) Field of Search ...................... 600/38–41; 606/118

(56) References Cited

U.S. PATENT DOCUMENTS

| | | | | |
|---|---|---|---|---|
| 2,238,660 A | * | 4/1941 | Santora | 606/118 |
| 2,345,639 A | * | 4/1944 | Tibone et al. | 606/118 |
| 2,355,209 A | * | 8/1944 | Dwoyer | 606/118 |
| 2,533,373 A | * | 12/1950 | Hinckley et al. | 606/118 |
| 2,620,800 A | * | 12/1952 | Powers | 606/118 |
| 2,646,046 A | * | 7/1953 | Maryan | 606/118 |
| 3,802,439 A | * | 4/1974 | Baumgarten | 606/118 |
| 3,874,389 A | * | 4/1975 | Baumgarten | 25/514 |
| D375,358 S | * | 11/1996 | Clark | D24/133 |

* cited by examiner

*Primary Examiner*—Samuel G. Gilbert (57) ABSTRACT

This device grips the skin of the penile shaft firmly, yet atraumatically, so that, as tension is applied to the device, new skin cells are stimulated to grow, gradually creating a new foreskin. The gripping device itself consists of two separate, unconnected, generally tapered gripping members. The larger end of the smaller, inner, member 11 is placed upon the glans penis 13, FIG. 4A. A double layer of skin 14, 15 is pulled up from the penile shaft and laid against this inner member, FIG. 4B. The outer gripping member 12 is then placed snugly but gently over this skin, FIG. 4C. Through a novel mechanism, which utilizes the unique gliding and everting function of the foreskin, as increasing tension is applied to the strut 16 attached to the inner member FIG. 4D, the two gripping members are drawn more tightly together, thus increasing the gripping pressure, FIGS. 3A, 3B.

19 Claims, 8 Drawing Sheets

FIG.IOA

FIG.IOB

FIG.IOC

FIG.II

FORESKIN RESTORATION DEVICE

CROSS REFERENCES TO RELATED APPLICATIONS

This application is entitled to the benefit of Provisional Patent Application Serial # 60/200,119, filed Apr. 27, 2000.

BACKGROUND

1. Field of Invention

This invention relates generally to gripping or clamping devices, and more particularly to devices which grip or clamp the skin. It also relates generally to stretching devices, and more particularly to devices which stretch the skin. It also relates to devices which promote expansion of skin through new skin growth.

2. Description of Prior Art

Although the idea of restoring foreskin may seem bizarre to some, there are many good reasons for doing so. Human beings show remarkable hubris in blithely cutting off something which it took mother nature millions of years to design. Some of the reasons for the existence of foreskin can be seen by comparing intact men with circumcised men. The foreskin of intact males produces pheromones—sexual stimulants—which have been proven to increase the man's attractiveness to others. Removing the foreskin also removes its natural gliding, "lubricating" function. Of women who expressed a preference, 90% favored sex with intact, rather than circumcised, men. Women are 40% more likely to have multiple orgasms with intact men. Not only his partners, but the male victim of circumcision himself also has greatly reduced sexual pleasure as the result of losing his foreskin. Besides losing millions of sensory nerve endings in the cut off skin, his unprotected glans is converted from a moist, glassy smooth, highly sensitive mucoid surface into a rough, dry, cornified structure with greatly reduced sensitivity.

Although routine infant male circumcision is still commonplace, its frequency is declining. This trend has been hastened, in part, by positions taken recently by two prestigious medical bodies in the United States. Although it had been claimed in the past that circumcision prevents many deaths from penile cancer, this research has been found flawed, and the American Cancer Society website currently has the following statement: "The consensus among studies that have taken these other factors into account is that circumcision is not of value in preventing cancer of the penis. It is important that the issue of circumcision not distract the public's attention from avoiding known penile cancer risk factors." Also, "As representatives of the American Cancer Society, we would like to discourage the American Academy of Pediatrics from promoting routine circumcision as preventative measure for penile or cervical cancer."

In 1998, the American Academy of Pediatrics issued a new policy statement which states, ". . . data are not sufficient to recommend routine neonatal circumcision. In circumstances in which there are potential benefits and risks, yet the procedure is not essential to the child's current well-being, parents should determine what is in the best interest of the child.

At present, there is no medical organization anywhere in the world which recommends routine male circumcision.

Although female circumcision has long been viewed with alarm as being a form of genital mutilation, the corresponding male genital mutilation of circumcision is often considered inconsequential, or even desirable.

The United States is the only industrialized nation which routinely circumcises male infants for non-religious reasons. The widespread American practice of routine infant male circumcision began between 1880 and 1920. In the widespread anti-sex atmosphere of that period, circumcision advocates pushed infant circumcision, claiming that it would prevent boys from masturbating, and further claiming to believe that by preventing masturbation, then one would also prevent many cases of brain tumors, epilepsy, diarrhea, etc. Although circumcision didn't stop masturbation, it did leave many males with a lifetime of impaired sexual enjoyment for both them and their partners. These are some of the reasons that some men have decided to restore their foreskins.

The methods of foreskin restoration presently available are quite limited. One method has been the creation of a new foreskin through surgical techniques. Donor skin is usually taken from the scrotum and attached to the penis so as to form a somewhat natural-appearing foreskin. This method has many disadvantages, which have caused it to fall into disfavor. Its use is discouraged by groups of men interested in restoration because of the following disadvantages. It is quite expensive, costing several thousand dollars. It has all the risks associated with surgery, including scarring, infection, hemorrhage, and risk of reactions to anesthesia. The transplanted skin does not have the characteristics of normal foreskin: It is wrinkled rather than smooth, has hair growing where it doesn't belong, and, being deprived of nerves, it lacks sensation. After surgery, there is a period of recovery during which the man cannot engage in sex. But the greatest disadvantage is that the surgically restored foreskin does not have the normal gliding action of the natural foreskin.

Organizations of men interested in foreskin restoration are unanimous in their recommendation that restoration be achieved through the application of tension to the skin of the penile shaft. Tension on skin does not merely stretch the skin, but, more importantly, it actually induces growth of new skin tissue.

Foreskin restoration through tension avoids the disadvantages of surgery and produces a foreskin which is nearly normal in both appearance and function. But, as generally employed, restoration through tension is very time consuming, generally taking several years to complete. It also has many other disadvantages, to be described below.

The most commonly employed method of restoration through tension involves applying tape to the skin of the shaft and pulling on it—via either an elastic band or by small weights hung from the tape. Since this method involves tape left on the penis for days at a time, it causes problems with spontaneous sex or showers in public places. Also, since stress is concentrated along the edge of the tape, skin tears are common. Furthermore, repeatedly applying and removing the tape is very irritating to the skin. The most commonly used tape configuration, called T-tape, requires that one get an erection before applying the tape. Needless to say, this greatly increases the inconvenience and time required for applying the tape.

In a search for foreskin restoration patents, the only patent found was U.S. Pat. No. 5,344,396, "Device for stretching the foreskin of the penis." This device has many disadvantages compared to this current application because:

1. It uses adhesive tape to secure the foreskin to the device, with all the above-mentioned problems with tape.
2. The device is essentially a large, cumbersome metal weight which would swing around while one walked, making it inappropriate for use in any public setting.

3. The device is so large that it would be very conspicuous under most clothing, and so, again, not suited for public use, and not suited to use during sleep because of discomfort if one rolled over on it during the night.

Another patent which has some superficial resemblance to the current application (although it has nothing to do with foreskin restoration) is U.S. Pat. No. 4,388,923, "External urinary drainage device." This device does have an inner member which fits over the glans, and an outer member which covers the pulled-up foreskin, which are features of the current application. However, there are many differences, specifically:

1. The "External Urinary Drainage Device" is used to collect urine, not expand foreskin.
2. The inner member is described as a "condom," or, alternatively, as being semirigid. In my device, the inner member is rigid.
3. The "External Urinary Drainage Device" is intended for use only with uncircumcised penises. My device is used only with circumcised penises.
4. In the "External Urinary Drainage Device," the outer member is firmly attached to the central drainage tube. In my device, the outer member is completely unattached to the central means for applying tension.
5. In the "External Urinary Drainage Device," the outer member is inverted and everted for application and removal of the device. In my device, the outer member is not inverted nor everted; it is simply slid onto the skin.

In my patent search, I found no other patents which even deserve comment, as they have no similarity to the present application.

There are several restoration devices described in the literature and websites devoted to restoration. These all require that there be more than enough skin so that it can be pulled down over, and at least one-quarter inch beyond, the tip of the glans, so that there is enough room for taping the drawn-forward foreskin with a ring of tape. At this stage, one device being used is a portion of a baby bottle nipple. The large part of the nipple is placed over the glans, the skin is drawn up over it and along the smaller nipple part. The skin is then taped with a tape ring. An elastic cord or small weight can then be attached to the nipple to provide gentle tension. As the foreskin progressively lengthens, the thin cap can be replaced by progressively thicker versions, often made of foam rubber, until one has a high domed structure between the glans and foreskin. Again, this method incurs all the disadvantages of tape, and allows only very low tension to be applied to the skin.

Another alternative involves a tiny dumbbell-shaped device, in which one end of the dumbbell is taped inside the foreskin, with the other end outside for some added weight. This device is sold commercially as "Foreballs."

There are a few other commercially available devices to aid foreskin restoration, in addition to the Foreballs mentioned above. These include the PUD (Penile Uncircumcision Device), which is a roughly cylindrical stainless steel device in which one end is hollowed out, to be positioned over the glans. The skin is then pulled up around the PUD and taped to it. Besides having the disadvantages involved with tape, this device is quite visible inside pants and swings around while walking. It is recommended that it not be worn at night, so tape must be applied and removed daily. It is also rather expensive.

Another device available commercially is called the RECAP EZ. It consists of a small plastic cone which sits on the glans, with the skin pulled up over the cone. An elastic band is then stretched and placed over the skin to hold it in place. To the tip of the cone is attached one end of a rubber tubing, the other end of which is attached to a sort of splint. (See attached photograph). The splint, which is made of rigid plastic, surrounds the base of the penis, extends along the bottom of the penis and several inches beyond its tip to where the end of the rubber tubing is fastened.

In use, this device is very uncomfortable unless it is allowed to project out from the body, so it cannot be worn in public or at night. It is uncomfortable to use, in part because of the elastic band. The elastic band is rather narrow, being only about one-quarter inch wide, and so it exerts rather high pressure because of its narrowness. To compound the problem with pressure, the elastic band must be stretched to apply it over the skin, so that it exerts pressure even when no tension is applied. Also, because the elastic band stretches more and more as more tension is applied to the rubber tubing, if more than about one pound of tension is applied, the cone pulls out through the hole in the elastic band, and the device simply falls off. Furthermore, in part due to the cone shape of the inner member which is placed over the glans, the device does not tolerate varying levels of tension, as would occur if the rubber tubing were attached to the leg, for example. It easily falls off under such conditions.

Another device, the Dual-action Incremental Longitudinally Expanding (DILE) Insert provides a mechanical method for providing mild tension by increasing the space between the glans and the foreskin, which is taped over the device (see diagram). As with other such space-filling methods, there are all the disadvantages of the tape, as well as the fact that the penis is made to at least appear to be smaller due to its being pushed back by the device.

The chief disadvantages of these devices include the time required for restoration (usually years), and the need to apply tape to the skin, with all the attendant disadvantages of tape mentioned above. Sometimes an elastic band is substituted for the tape, but this has the disadvantage that, if it is tight enough to hold the skin securely, then it cuts off blood flow. Also, these devices allow only minimal tension to be applied to the skin because, with higher tension, either skin tears occur along the tape edge, or the device slips off, or both.

There exists another, far more rapid method of skin expansion which is used by plastic surgeons to provide large amounts of skin for reconstructive surgery and to cover skin defects resulting from removal of large skin lesions such as cancer. When used surgically, a heavy rubber balloon is first implanted under normal skin where the expansion is desired. Then saline is injected under pressure into the balloon, and left in place. Perhaps every two days, more saline is injected. Responding to the skin tension over the balloon, new skin cells grow, creating additional skin tissue, with a consequent lowering of tension on the skin. Using this method, providing an amount of skin similar to that needed for foreskin restoration takes only a few weeks, rather than the years generally required for restoration using current techniques.

It would appear that if one could more closely duplicate the parameters of tension and time involved in surgical skin restoration, then foreskin restoration should be dramatically accelerated.

SUMMARY

In accordance with the present invention, a skin gripping device, consisting of an inner and an outer gripping member, for applying tension to the skin of the shaft of a circumcised penis. The space formed between these two gripping members is approximately uniform and approximately the thickness of the double layer of skin which they grip when they are pressed together. In response to the stimulus provided by skin tension, new skin grows, and the result is a new foreskin which approximates the original in structure and function.

Objects and Advantages

Accordingly, several objects and advantages of my invention are:

a) Extreme ease and speed of attaching (10 seconds) and removing (2 seconds) the device from the penis.
b) No tape or anything else remains on the skin, which allows showers in semi-public areas, as well as spontaneous sex.
c) In contrast to T-tape, no need to get an erection before applying the device.
d) Much more comfortable than other methods because the gripping force is distributed over a larger area.
e) No taste.
f) Can be worn day and/or night.
g) Inconspicuous with ordinary loose-fitting clothing.
h) The inner gripping member provides an occlusive covering for the glans, thereby creating a moist environment which encourages the transformation of the cornified epithelium back to its natural state of being a mucous membrane with a thin, sensitive epithelium.
i) The gripping force automatically changes with need, being stronger with greater tension, and weaker with less tension, and virtually zero when no tension is applied.
j) Because the outer gripping member undergoes very little expansion when tension is applied to the inner member, quite high tensions (up to fifteen pounds for short periods) can easily be achieved, without having the inner member pull out through the hole in the outer member.
k) More rapid foreskin expansion is possible because greater tension is both feasible and comfortable.
l) By applying counter tension to the strut, the gripping pressure is automatically reduced. This can even be done through one's clothing to relieve any discomfort or to remove the device quickly.
m) Due to the attached wings, it is easy to push or pull on the end of the strut, either directly or through one's pants. Pushing on the strut reduces clamping pressure, to ease removal or relieve discomfort. By intermittently pulling strongly on the wings, one can achieve high skin tension, which has recently been shown to greatly accelerate skin expansion.

THE FIGURES

In the drawings, closely related figures have the same number but different alphabetic suffixes.

In FIG. 3A, the inner member 11 has been placed upon the glans 13, the double foreskin layer is pulled up against the inner member, and the outer member is placed lightly upon the skin. Index marks show the position of the inner and outer foreskin layers. In FIG. 3B, tension has been applied to the wire strut and inner member This causes the inner layer of foreskin 15 to be drawn to the left and to become more everted, while the outer layer of foreskin remains stationary against the outer member This causes the inner member and foreskin to be pulled tightly into the outer member, thereby producing a clamping pressure upon the foreskin.

In FIG. 4A, the inner member 11 has been placed upon the glans. In FIG. 4B, skin from the shaft 14 has been pulled up and laid upon the inner member 11. In FIG. 4C, the outer member 12 has been placed upon the skin. In FIG. 4D, tension has been applied to the wire strut, and the skin has been pulled to the right, beyond the glans.

DETAILED DESCRIPTION AND USE OF PREFERRED EMBODIMENT, WITH REFERENCE TO FIGURES

In FIGS. 1 through 4D are shown the inner gripping member 11 and outer gripping member 12 of the device. The inner member 11 has approximately the size and shape of one half of the shell of a very small hen's egg and is relatively rigid. At or near the tip of this inner "shell" is attached a rigid or semirigid rod or strut 16. At the end of the strut can be attached a cord or band as a means of applying tension to the inner shell. The device in actual use is shown in FIGS. 2 through 4D.

Figure 4A:
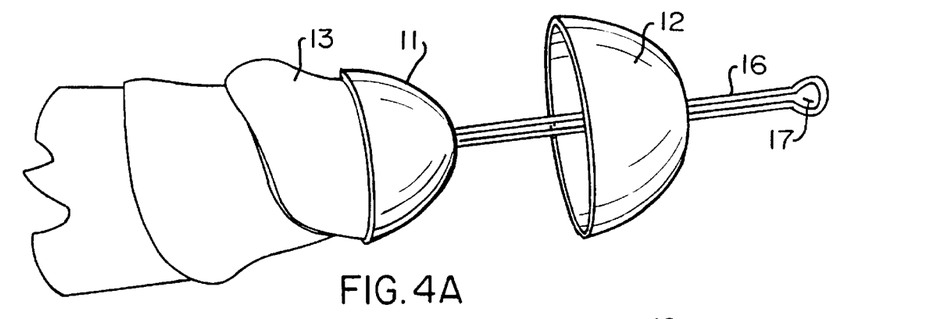
FIGS. 4A to 4D show in detail how the device is applied and operated.
Figure 4B:
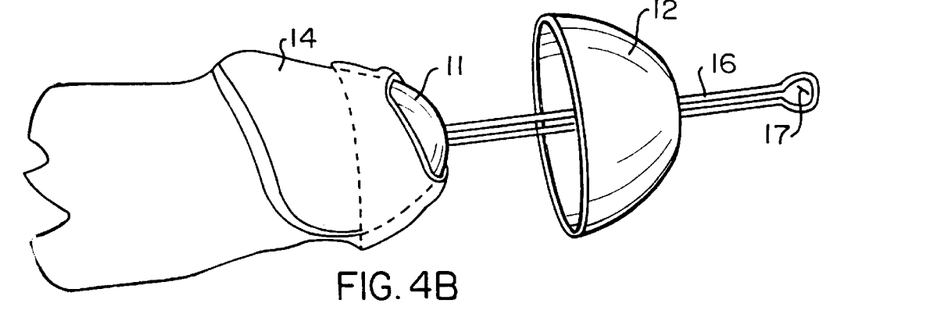
Figure 4C:
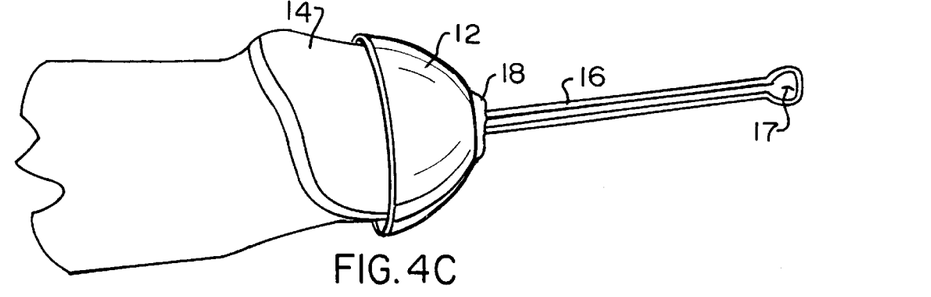
Figure 4D:
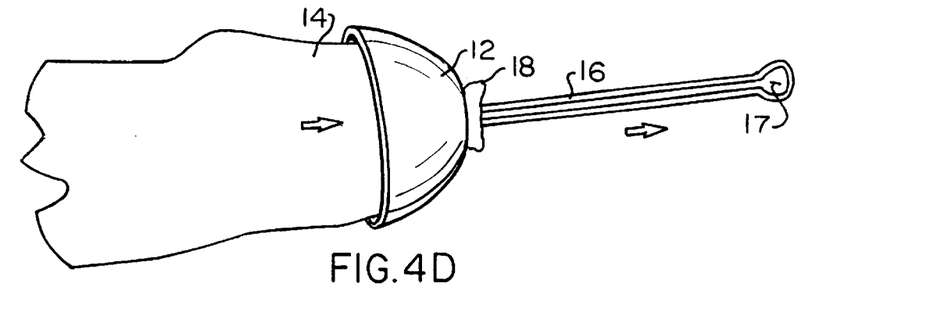
Figure 5A:
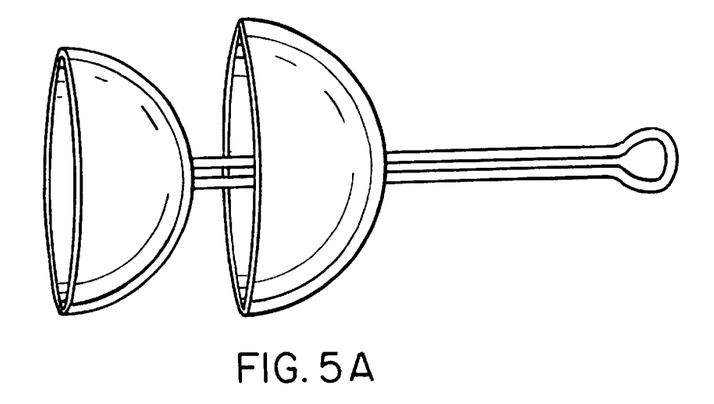
FIG. 5A shows the alternative embodiment of hemispheric inner and outer members.
Figure 5B:
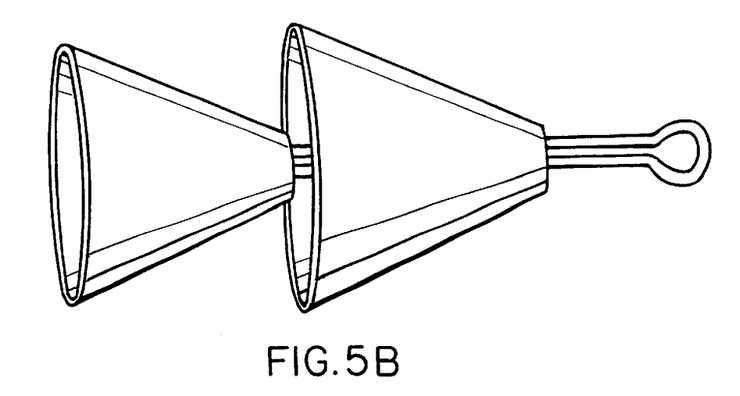
FIG. 5B shows the alternative embodiment of conical inner and outer members.

The open end of this half shell 11 is placed over the glans penis 13, FIG. 4A, so as to partially or fully cover it. The skin 14,15 of the penile shaft just below the glans is then pulled part way up against the outer surface of the shell, FIG. 4B and held in place with the fingers. The second, outer gripping member 12 is also approximately the shape of half an egg shell, but is flexible, minimally stretchable, and a little larger so that it will fit snugly over the skin which has just been pulled up to cover the lower portion of the inner shell. This outer shell has an opening (from approximately one-fifth to three-quarters inch in diameter) at its small end, through which the wire strut can move freely.

When in use, the space between the two gripping members is, at least in part, approximately uniform and equal to the thickness of the double layer of foreskin between them. The result is a nearly uniform pressure over a relatively large area. This reduces the chance of pressure points and increases comfort.

The outer shell is actually detached from other parts of the device; however, it functions in a rather surprising manner when it is placed snugly over the skin which was pulled up over the inner shell and tension is applied to the wire strut. By applying increasing tension to the strut, the outer shell of the clamp is actually drawn ever more tightly against the skin, so that as the tension increases, so too does the clamping pressure.

Figure 9A:
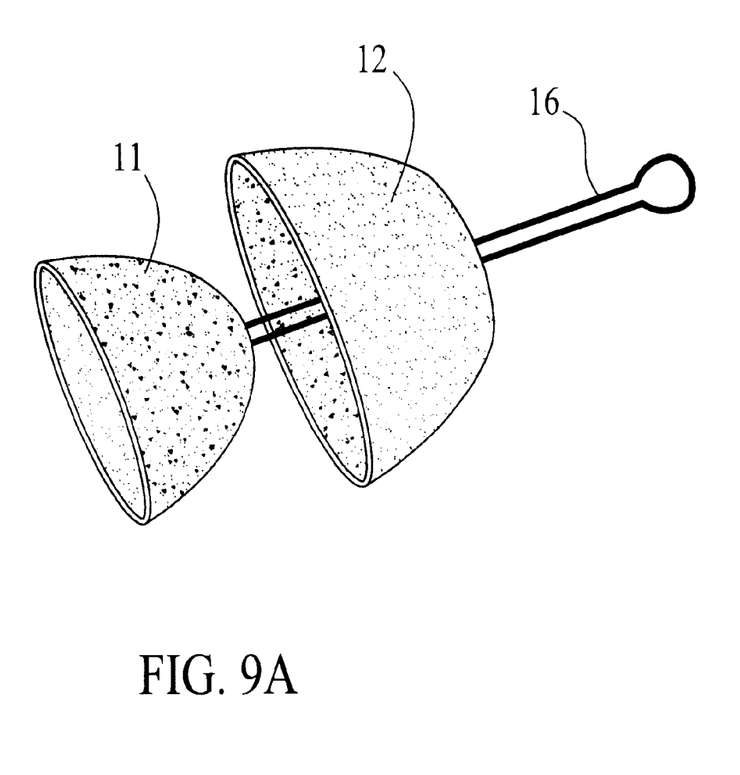
FIG. 9A shows roughened gripping surfaces (the outer surface of the inner member and the inner surface of the outer member).
Figure 9B:
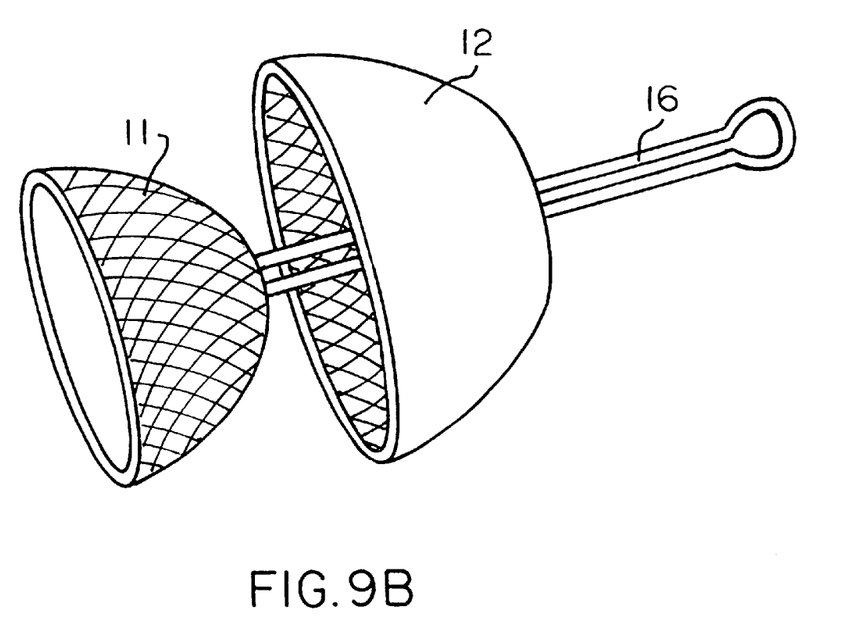
FIG. 9B shows ribbed gripping surfaces (the outer surface of the inner member and the inner surface of the outer member).

This rather unexpected result can be explained as follows. First of all, both of these two clamping surfaces 11,12 which hold the skin 14,15 between them (the outer surface of the inner shell and the inner surface of the outer shell) have surfaces which do not allow easy sliding of the skin over them (they may be rough, FIG. 9A, covered with rubber, or ribbed, FIG. 9B, for example). Now, let us suppose that the inner shell has been placed over the glans, FIG. 4A, the double layer of skin has been pulled up over it, FIG. 4B, and the outer shell placed snugly over the skin, FIGS. 3A and 4C.

Figure 1:
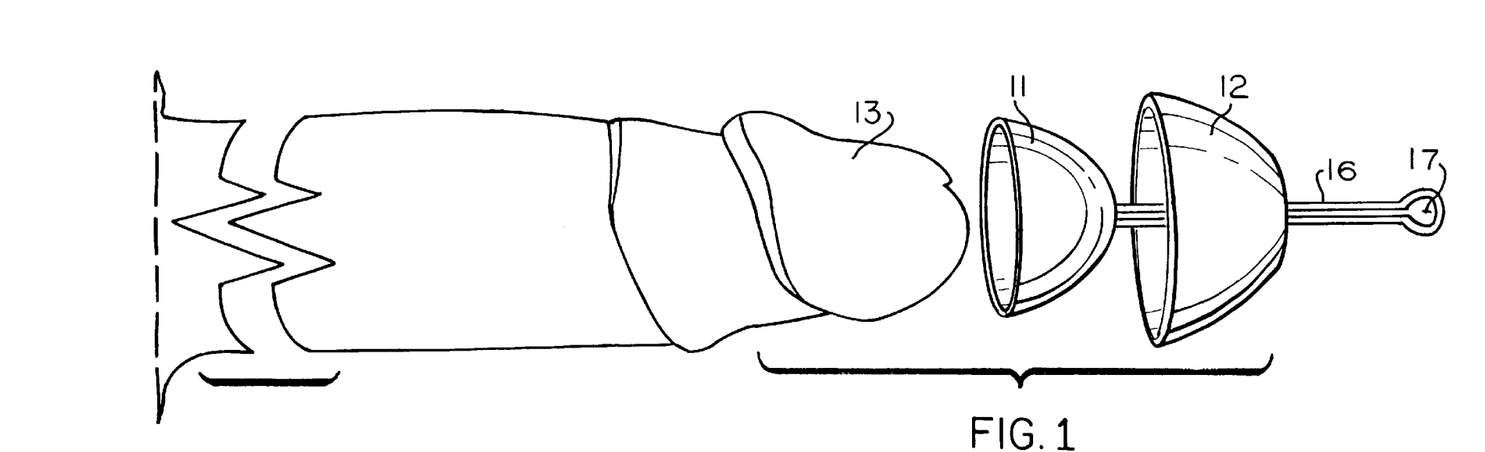
FIG. 1 shows a perspective view of a circumcised penis and the preferred embodiment.
Figure 2:
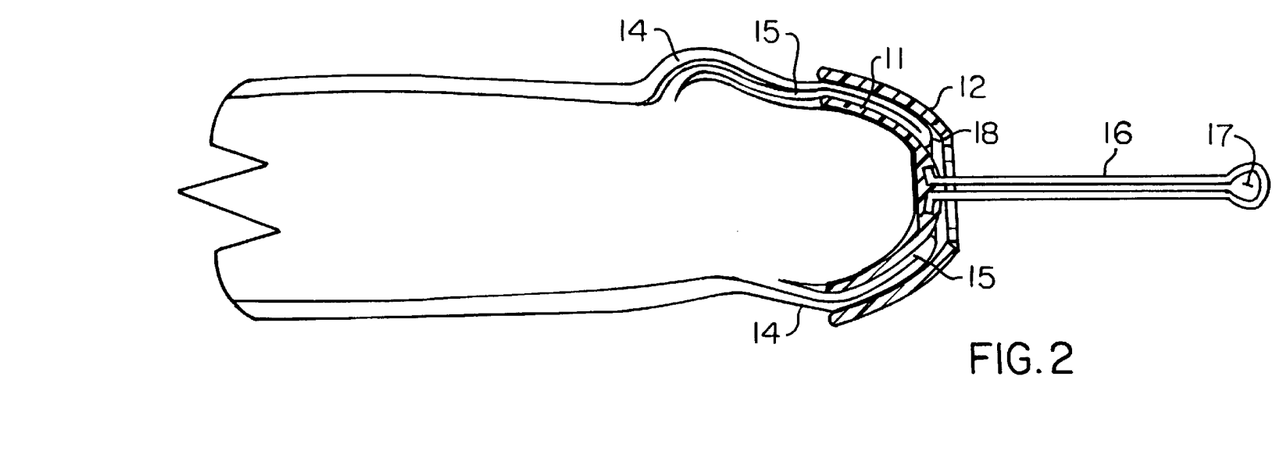
FIG. 2 shows the device in use, applied to the penis, with a double layer of foreskin clamped between the inner and outer gripping members.
Figure 3A:
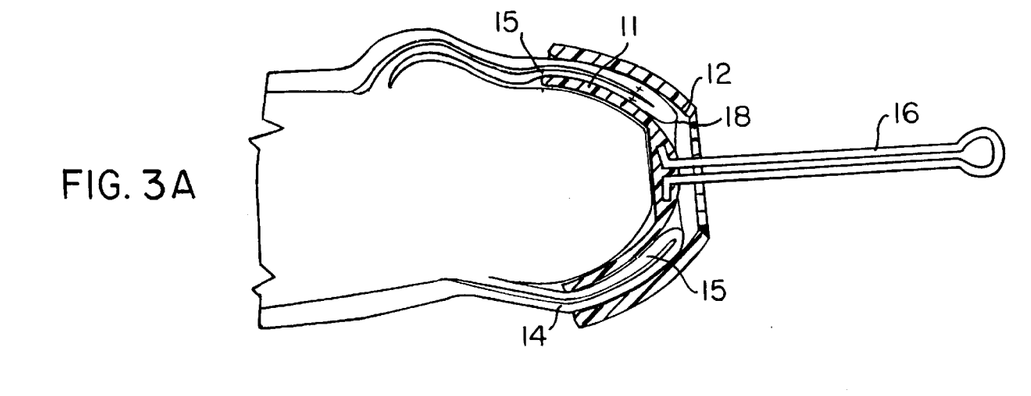
FIGS. 3A and 3B show what happens when tension is applied to the inner member 11 via the wire strut 16.
Figure 3B:
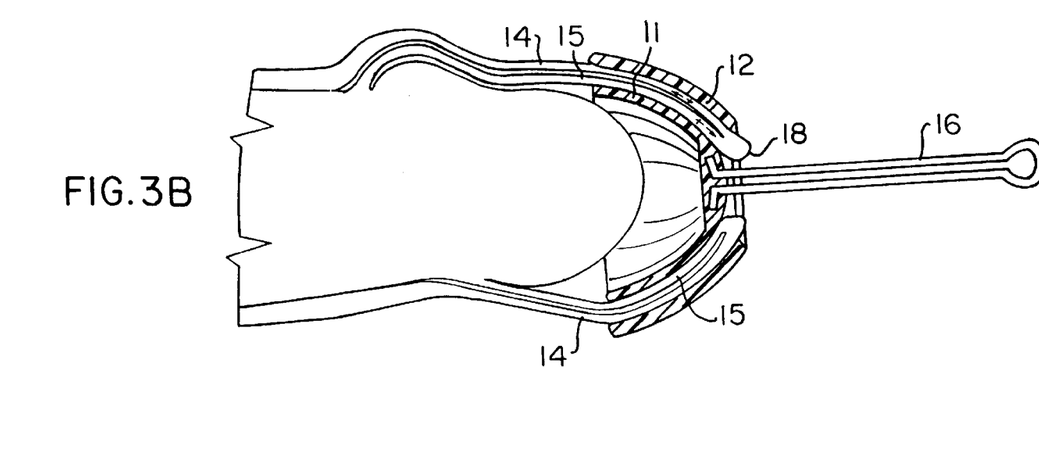

Now consider what happens when the wire strut (attached only to the inner shell) is pulled, FIG. 3B. [The crucial point here is what happens along the distal edge 18 of the skin lying on the inner shell, where the skin is folded back.] The way in which the skin moves can be seen by observing the index marks on the two layers of skin in FIGS. 3A and 3B. The outer layer of skin 14 on the upper surface of the penis extends back to the abdominal wall, where it is firmly attached 19. Due to this attachment, this outer layer of skin, along with its covering outer shell, does not move significantly when the wire strut is pulled; yet, at the same time, the inner shell, along with its covering inner layer of skin 15, does move distally, away from the body. This causes the index mark on the inner skin layer 15 to move distally relative to the outer skin layer 14.

This progressive eversion allows the inner shell to move distally into the stationary outer shell, so that the outer shell forms a sort of stationary socket into which the inner shell, along with its covering skin, is pulled by tension on the strut. And, because of the tapered shape of the two shells, this results in an increased clamping pressure. In other words, the harder one pulls on the strut, the more strongly the clamp grips the skin.

The reason that a shape for the shells which approximates half an egg shell is preferred is seen in practice because it stays in place well, even if there are wide variations in the amount of tension on the strut.

The strut attached to the inner shell serves the following purposes. The primary purpose of the strut is to provide a means for applying counter traction to the inner shell when the device is in use. This causes an immediate relaxation of the gripping pressure upon the skin, to facilitate removal of the device or to relieve discomfort resulting from too much tension. The strut also facilitates application of the device to the skin by stabilizing the inner shell so that the skin can more easily be pulled up over it. In addition, by bending a strut made of stiff wire, one can relieve pressure points which can occur on the skin between the strut and the outer shell.

Alternative Embodiments

Figure 6A:
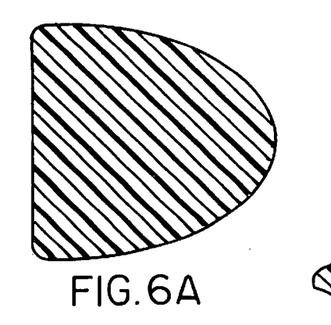
FIGS. 6A through 6C show the alternative embodiments of solid and partially solid inner members.
Figure 6B:
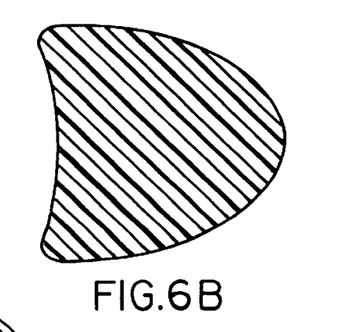
Figure 6C:
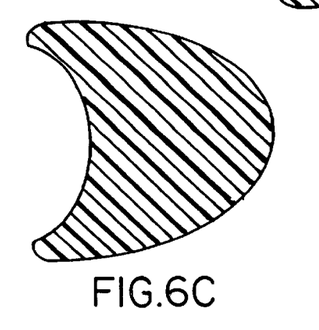
Figure 7A:
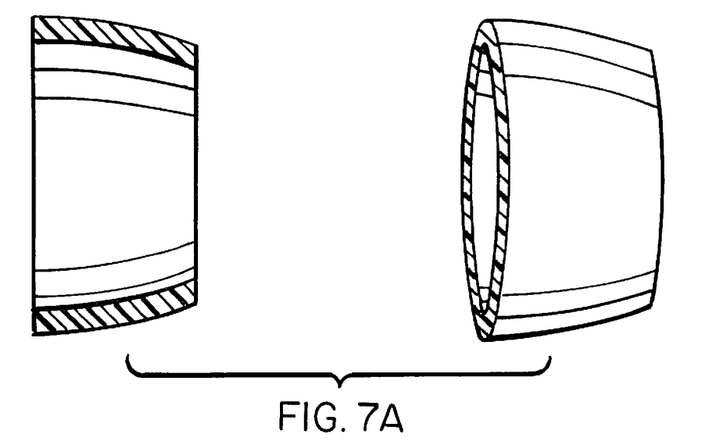
FIGS. 7A and 7B show the alternative embodiments of narrower outer members.
Figure 7B:
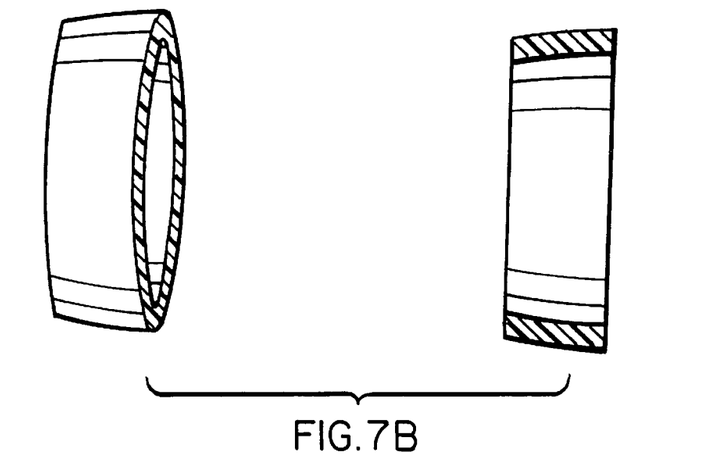
Figure 10A:
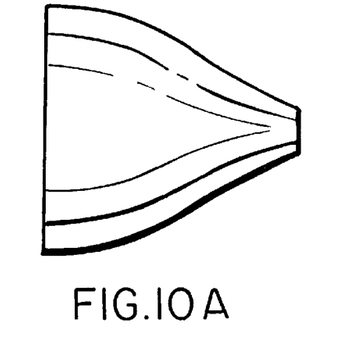
FIGS. 10A through 10C show compound shapes consisting, respectively, of a truncated cone and paraboloid, a hemisphere and cylinder, and a paraboloid and cone.
Figure 10B:
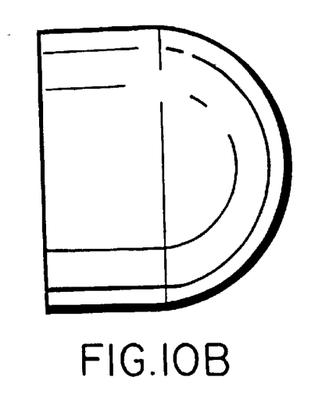
Figure 10C:
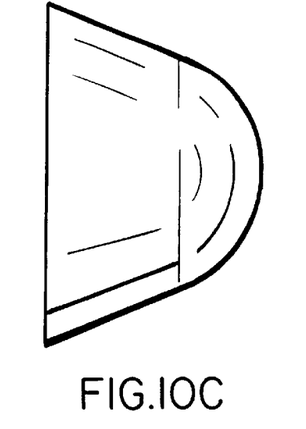

Instead of being simply the shape of a paraboloid, cone or hemisphere, the outer, clamping surface of the inner member could be some combination of these, as well as being partially cylindrical. Since there are an infinite number of possible variations resulting from such combinations, only a few representative examples will be shown, and these only in outline, FIGS. 10A to 10C. FIG. 10A shows a compound shape consisting of a truncated cone plus a paraboloid. FIG. 10B is a hemisphere plus a cylinder, and FIG. 10C is a paraboloid plus a truncated cone. Rather than being a thin shell, the inner clamping member could be either solid or partially hollowed out, FIGS. 6A to 6C. It could be rigid or semirigid.

Figure 8:
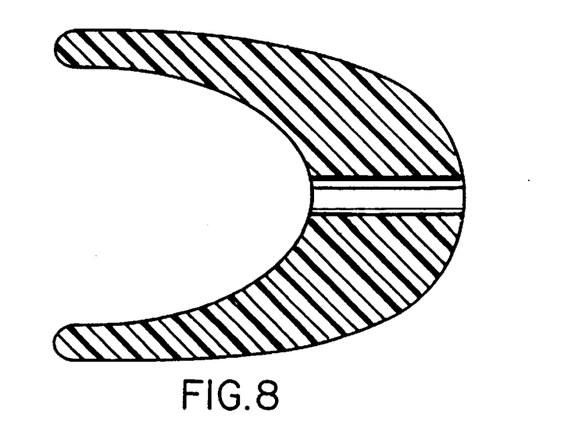
FIG. 8 shows the alternative embodiment of a thicker outer shell.

The outer member could be thicker than that described for the preferred embodiment. It could, for example, consist of a flexible foam cap having an opening of the proper shape to fit over the skin which has been laid upon the inner shell, FIG. 8.

Figure 11:
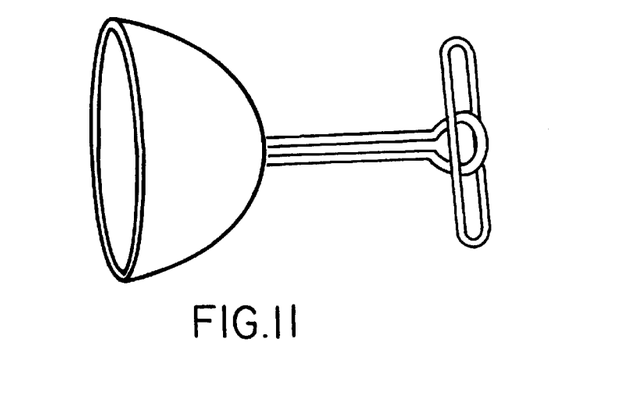
FIG. 11 shows wings, 20, attached to the free end of the strut.

The strut attached to the inner element could be provided with an attached protuberance at its free end to facilitate pushing or pulling on the strut, which could even be done through one's clothing. Pushing on the strut allows one to both relieve discomfort resulting from too much tension and to remove the device more easily. Pulling on the strut allows one to temporarily apply increased tension in order to speed skin expansion. The protuberance attached to the end of the strut could take on the form of small wings, FIG. 11, which would lie flat against the underlying skin during use. The strut could be made of various materials other than insulated electrical wire. It could, for example, be an uninsulated metallic wire or rod, or made of plastic or wood. Alternatively, the wire strut could be eliminated entirely, and a cord or band could be attached directly to the inner shell.

Method of Manufacture

The several components of this invention can be manufactured in a rather straight forward manner. The relatively rigid inner member can be injection molded from such thermoplastic materials as ABS (acrylonitrile-butadiene-styrene), polycarbonate, or even polystyrene (although the brittleness of polystyrene may be a disadvantage), or molded, for example, from rigid polyvinyl chloride or polyester or a thermoset rather than thermoplastic. It could even be machined from such materials as wood or metal. Because of its toughness and relatively low price and ease of molding, ABS would seem to be the preferred material.

The semi-rigid strut which extends from the tip of the inner member could be made from such materials as plastic, wood, or, preferentially, from a length of insulated electrical wire. The preferred configuration consists of a 6½ inch length of 14 gauge insulated electrical wire. Approximately ½ inch of the insulation is removed from each end, the wire is folded at its middle, the ends are twisted one turn about each other, and the tips are then curved into a ¼ inch spiral. The doubled-over end is then inserted through a hole drilled in the tip of the inner member from the inside, so the twisted tips are inside the small end of the member. To hold the wire in place and reinforce the tip of the member, a small amount of adhesive material such as epoxy resin is poured into the member's tip and allowed to harden with the member placed small end down. The twisted wire ends are entirely covered by the epoxy, which occupies only about ¼ of the member's length at its tip.

After the entire inner and outer surfaces of the inner member, as well as the surface of the reinforcing epoxy resin, are roughened by sanding, a slip-resistant coating may be applied to the member in several possible ways, such as dipping, brushing, or spraying on such materials as latex, urethane rubber, or soft vinyl such as Plasti-Dip.

The outer member, which is thinner and more compliant than the inner member, is preferentially dip, injection, or rotationally molded from soft vinyl or a vinyl plastisol. Although it could be molded from an elastomer such as latex, urethane or silicone rubber, its elastic compliance must be carefully controlled, so that it will stretch very little when the inner member is pulled by the elastic cord, and be sufficiently rigid to prevent the inner member from pulling out through the opening in its small end. In its preferred configuration, the opening in the small end of this member is approximately one-half to three-quarters of an inch in diameter. In other configurations, it may be as small as 3/16" in diameter.

The other parts of the invention can readily be purchased at stores. The elastic cord could preferentially be made from, for example, 1/8" or 3/16" shock cord, available from marine supply stores. A flat elastic band of the type used in sewing could also be used, as could a plain rubber cord. The elastic cord can be attached to a stocking or garter by means of a device called a "drop loop," sold at sewing supply stores, or by a suspender clip. The wings at the end of the strut could be made of metal, plastic, wood, or similar materials. Due to its high strength and toughness, polycarbonate would probably be the preferred material for this structure.

What is claimed is:

1. A device for gripping the skin of the shaft of a circumcised penis, consisting of:
    a. an inner gripping member having:
        i) a generally tapered convex surface, including a tip, and
        ii) an attached means at or near the tip for applying tension, and
    b. an outer gripping member which:
        i) is functionally related to said inner member, yet has no force-transmitting connection to it, and
        ii) has a concavity that conformingly receives the inner member, over substantially the entire length of the inner member, and
        iii) is constructed of a material having an elastic compliance such that the member's circumference increases less than five percent when a stress of up to ten pounds is applied to it, and
        iv) has an opening through which passes said attached means of the inner member;
    the entire device being of such a size that it is inconspicuous when worn under clothing; wherein a double layer of penile shaft skin may be gripped between the inner and outer members.

2. The device of claim 1 wherein the convex surface portion of the inner gripping member has the general shape of a truncated paraboloid, and the concavity of the outer gripping member is generally complementary to the convex surface portion of the inner gripping member.

3. The device of claim 1 wherein the convex surface portion of the inner gripping member has the general shape of a truncated cone, and the concavity of the outer gripping member is generally complementary to the convex surface portion of the inner gripping member.

4. The device of claim 1 wherein the convex surface portion of the inner gripping member has the general shape of a hemisphere, and the concavity of the outer gripping member is generally complementary to the convex surface portion of the inner gripping member.

5. The device of claim 1 wherein a portion of both the concave surface of the outer gripping member, and the convex surface of the inner gripping member, are respectively, formed into frictional surfaces to enhance gripping.

6. The device of claim 1 wherein the inner member has been to some degree hollowed out to form a sort of shell, whose open end is placed over the glans penis, so that at least a portion of the glans fits inside the inner member.

7. The skin clamping device of claim 1 wherein the inner member is sufficiently rigid so that it is not significantly deformed when in use, nor during application and removal.

8. The device of claim 1 wherein the inner member has intermediate rigidity, so that it is not significantly deformed when in use, but can be folded side-to-side to facilitate its application and removal, so that the foreskin is minimally stretched thereby.

9. The device of claim 1 wherein the outer member is relatively thin, being between one-thousandth and one-half inch thick, and is sufficiently flexible so that it conforms to the skin surface over which it is placed.

10. The device of claim 1 wherein the inner member has a compound shape which is a combination of two or more shapes selected from the group consisting of paraboloid, cone, hemisphere, and cylinder.

11. The device of claim 1 wherein the inner and outer gripping members are constructed of a synthetic plastic material.

12. The device of claim 1 which has a strut that has a proximal end portion attached at or near the tip of the inner member, and a distal end portion extending out from the inner member, wherein said strut is of sufficient rigidity so that a force applied to its distal end portion will allow the inner member to be moved.

13. The strut of claim 12 which is malleable, allowing the strut to be bent.

14. A device for gripping the skin of the shaft of a circumcised penis comprising:
    a. an inner gripping member having:
        i) a generally tapered convex surface, including a tip, and
        ii) an attached means at or near the tip for applying tension, and
    b. an outer gripping member which:
        i) has a concavity which conformingly receives the inner member, and
        ii) is constructed of a material having an elastic compliance such that the member's circumference increases less than five percent when a stress of up to ten pounds is applied to it;
    whereby a double layer of penile shaft skin may be gripped between the inner and outer members, and
    wherein a portion of both the concave surface of the outer gripping member, and the convex surface of the inner gripping member, are, respectively, formed into frictional surfaces to enhance gripping, in which the frictional surfaces are ribbed.

15. A device for gripping the skin of the shaft of a circumcised penis comprising:
    a. an inner gripping member having:
        i) a generally tapered convex surface, including a tip, and
        ii) an attached means at or near the tip for applying tension, and
    b. an outer gripping member which:
        i) has a concavity which conformingly receives the inner member, and
        ii) is constructed of a material having an elastic compliance such that the member's circumference increases less than five percent when a stress of up to ten pounds is applied to it;
    whereby a double layer of penile shaft skin may be gripped between the inner and outer members, wherein a portion of both the concave surface of the outer gripping member, and the convex surface of the inner gripping member, are, respectively, formed into frictional surfaces to enhance gripping, in which the frictional surfaces are scored.

16. A device for gripping the skin of the shaft of a circumcised penis comprising:
   a. an inner gripping member having:
      i) a generally tapered convex surface, including a tip, and
      ii) an attached means at or near the tip for applying tension, and
   b. an outer gripping member which:
      i) has a concavity which conformingly receives the inner member, and
      ii) is constructed of a material having an elastic compliance such that the member's circumference increases less than five percent when a stress of up to ten pounds is applied to it; whereby a double layer of penile shaft skin may be gripped between the inner and outer members, and
   wherein a portion of both the concave surface of the outer gripping member, and the convex surface of the inner gripping member, are, respectively, formed into frictional surfaces to enhance gripping, in which the frictional surfaces are coated with rubber, or other material having a high coefficient of friction.

17. A device for gripping the skin of the shaft of a circumcised penis comprising:
   a. an inner gripping member having:
      i) a generally tapered convex surface, including a tip, and
      ii) an attached means at or near the tip for applying tension, and
   b. an outer gripping member which:
      i) has a concavity which conformingly receives the inner member, and
      ii) is constructed of a material having an elastic compliance such that the member's circumference increases less than five percent when a stress of up to ten pounds is applied to it;
   whereby a double layer of penile shaft skin may be gripped between the inner and outer members, and including a strut that has a proximal end portion attached at or near the tip of the inner member, and a distal end portion extending out from the inner member, wherein said strut is of sufficient rigidity so that a force applied to its distal end portion will allow the inner member to be moved, yet is malleable, allowing the strut to be bent, and whereby the strut is made from a doubled-over insulated or non-insulated metallic wire having its free ends anchored at or near the tip of the inner member.

18. A device for gripping the skin of the shaft of a circumcised penis comprising:
   a. an inner gripping member having:
      i) a generally tapered convex surface, including a tip, and
      ii) an attached means at or near the tip for applying tension, and
   b. an outer gripping member which:
      i) has a concavity which conformingly receives the inner member, and
      ii) is constructed of a material having an elastic compliance such that the member's circumference increases less than five percent when a stress of up to ten pounds is applied to it;
   whereby a double layer of penile shaft skin may be gripped between the inner and outer members, and including a strut that has a proximal end portion attached at or near the tip of the inner member, and a distal end portion extending out from the inner member, wherein said strut is of sufficient rigidity so that a force applied to its distal end portion will allow the inner member to be moved, and further including a protuberance at or near its free end, to act as a grip or handle; said protuberance is in the form of small wings, which are approximately ½" long by 3/16" diameter.

19. A method for restoring the foreskin of a circumcised male comprising the following steps
   a. selecting a generally tapered inner member for gripping the skin, said inner member having:
      i) a size such that it may be positioned upon or over the glans penis, with its larger end more proximal toward the man's body, so that a double layer of skin from the penile shaft may be pulled up and laid against the inner member, to form, in effect, a foreskin, and
      ii) an attached means at or near its tip for applying tension, and
   b. selecting a covering or outer member for gripping the skin, said outer member having:
      i) a size and shape which allows it to fit snugly yet gently, without stretching, over at least part of said double layer of skin which has been pulled up against the inner member, and
      ii) very low elastic compliance, so that its circumference increases less than five percent when a stress of up to ten
   whereby, when
      i) the inner member has been placed upon or over the glans, and
      ii) the skin has been pulled up over the inner member, and
      iii) the outer member has been placed upon the skin;
   there is no pressure applied to the skin by the outer member; only after tension has been applied to the inner member, by way of said means for applying tension, does the pressure applied to the skin between the inner and outer member increase, and then it increases proportionately to said tension, by a mechanism which exploits the unique everting and gliding function of the foreskin, whereby the skin is gripped only as tightly as it must be for any given level of tension, thereby insuring maximum comfort of the device.

* * * * *